United States Patent
Logue

[19]

[11] Patent Number: 5,909,118
[45] Date of Patent: Jun. 1, 1999

[54] COMBINATION OF A FLUX COUPLING COEFFICIENT, A RESONANT PICK-UP COIL CIRCUIT AND A DRIVING FREQUENCY SPECTRUM FOR INCREASING THE SPATIAL RESOLUTION OF POLAR COORDINATES SENSORS

[76] Inventor: Delmar L. Logue, Box 60, Herrick, Ill. 62431

[21] Appl. No.: 08/832,100

[22] Filed: Apr. 3, 1997

Related U.S. Application Data

[63] Continuation-in-part of application No. 08/599,775, Feb. 12, 1996, Pat. No. 5,793,204, and a continuation-in-part of application No. 08/685,854, Jul. 24, 1996, Pat. No. 5,754,043.

[51] Int. Cl.[6] .......................... G01N 27/72; G01N 27/90
[52] U.S. Cl. ......................... 324/240; 324/228; 324/232
[58] Field of Search ...................... 324/207.17–207.19, 324/228, 232, 233, 239, 240

[56] References Cited

U.S. PATENT DOCUMENTS

| | | | |
|---|---|---|---|
| 4,282,487 | 8/1981 | Warren et al. | 324/204 X |
| 5,404,101 | 4/1995 | Logue | 324/207.17 |
| 5,418,460 | 5/1995 | Cloutier et al. | 324/207.17 X |
| 5,532,591 | 7/1996 | Logue | 324/232 X |
| 5,548,212 | 8/1996 | Logue | 324/233 X |
| 5,554,933 | 9/1996 | Logue | 324/233 |
| 5,559,432 | 9/1996 | Logue | 324/207.17 |
| 5,574,367 | 11/1996 | Logue | 324/207.17 X |

*Primary Examiner*—Gerard Strecker

[57] ABSTRACT

A combination of three factors for increasing the spatial resolution of a polar coordinates sensor. (1) a coefficient of coupling factor including a gap in the magnetic circuit path between the driving core and the pick-up core. (2) a tuned "tank-circuit" factor including a capacitor connected in shunt with the pick-up coil. (3) a driving frequency spectrum factor for modulating the frequency of the sine-cosine excitation to the driving core.

1 Claim, 6 Drawing Sheets

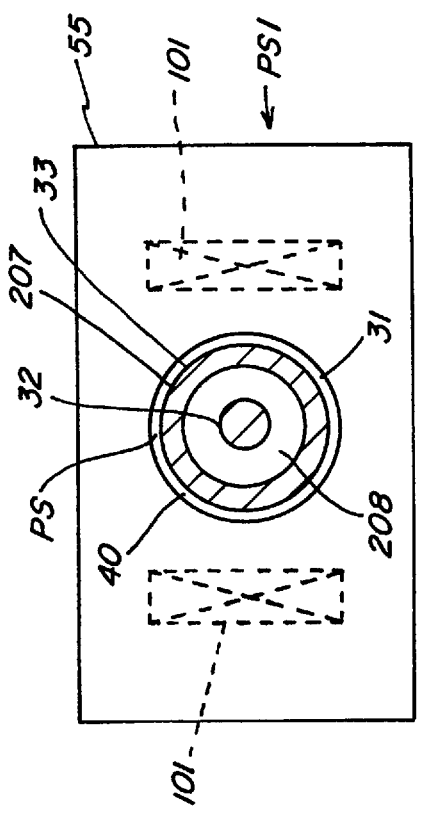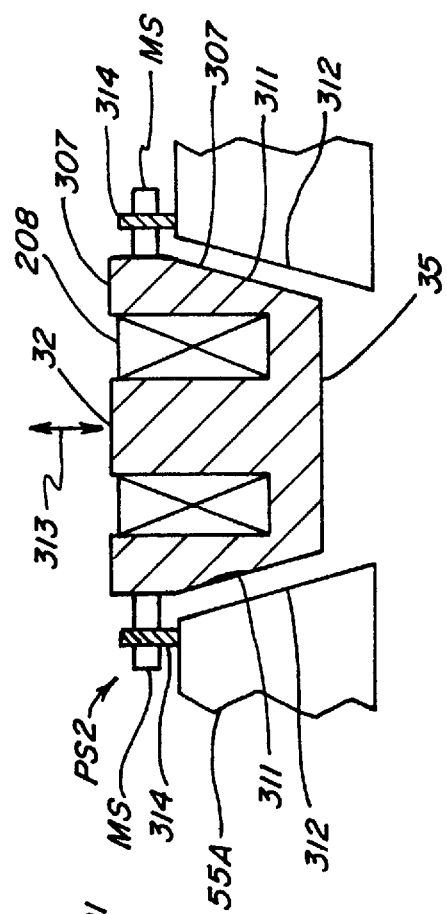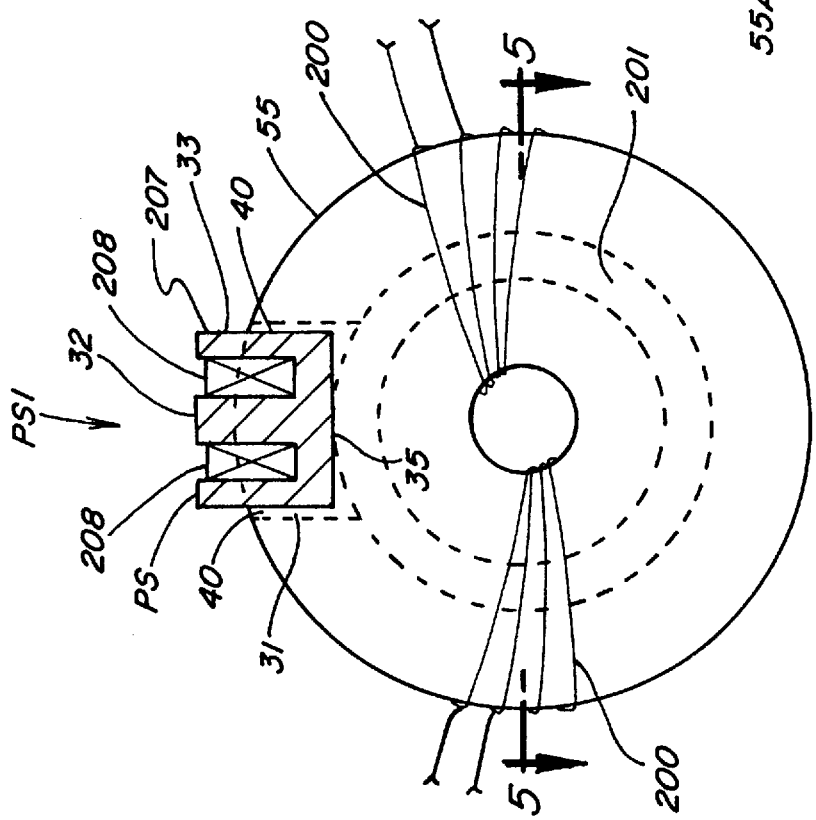

COMBINATION OF A FLUX COUPLING COEFFICIENT, A RESONANT PICK-UP COIL CIRCUIT AND A DRIVING FREQUENCY SPECTRUM FOR INCREASING THE SPATIAL RESOLUTION OF POLAR COORDINATES SENSORS

RELATED PATENT APPLICATIONS

This Patent Application is a continuation-in-part of the following Patent Applications:

Ser. No. 08/599,775 filed Feb. 12, 1996, now U.S. Pat. No. 5,793,204 and Ser. No. 08/685,854 filed Jul. 24, 1996, now U.S. Pat. No. 5,754,043. Further background is contained in Disclosure Document Nos. 371371, filed Feb. 3, 1995, 387120, 401663, filed Jun. 17, 1996, 402480, filed Jul. 12, 1996, 406005, filed Sep. 20, 1996.

This invention relates to all the rotating magnetic field sensor devices in the above related patents, and in particular to a combination of three basic factors that affect the resolving power of the polar coordinates sensor.

The conventional eddy current sensor probe is beset by two inherent sources of signal error: (a) "lift-off" gap between the probe and the test article and (b) gap variations between layers such as variable gapping found between the skins of an aircraft splice joint. Due to variable gapping between the layers, second layer flaw signals obtained with single frequency eddy current instruments are confounded with gap signals.

SUMMARY

Continued research has revealed, there are three basic factors that greatly affect the spatial resolution of all the polar coordinate sensors disclosed in the above related patents.

1. A critical coupling coefficient between the driving core and the pick-up core.
2. A resonant "tank" (series resonant circuit) in the pick-up coil circuit.
3. Frequency modulation of the sine-cosine currents supplied to the driving core.

These three factors combined in the right proportion make possible an eddy current probe having multi-layer flaw resolution i.e. distinct signal components indicating in which layer flaw is located.

Furthermore, variations in probe lift-off or gapping variations between layers does not change the waveshape of the first and/or second layer flaw components. The axis of the sensing face may be tilted several degrees out of perpendicularity to the plane of the first layer without loss of the second layer flaw waveshape.

Frequency modulation of the sine-cosine currents exciting the polar sensor driving core has the effect of changing the angular velocity of the rotating magnetic moments within the driving core. In essence the outer cylindrical pole of the driven pick-up core becomes a spinning magnetic dipole having diameter-wise north and south poles.

This angular velocity change may be either a positive acceleration or a negative acceleration (frequency ramping up or ramping down).

This driving frequency modulation may take several forms: (1) Linear ramping up of the sine-cosine excitation frequency over a predetermined range. (2) Linear ramping down of the sine-cosine excitation frequency over a predetermined range.

A unique form of eddy current sub-frequency conversion takes place as the driving flux passes through the first layer when the angular velocity of the sensing pattern is changing. This frequency modulation factor may be called Variable Angular Velocity (VAV). It is believed a critical flux coupling coefficient enhances this sub-frequency conversion process by allowing the pick-up core to ring at frequencies lower than the driving frequency.

This sub-multiple signal frequency conversion process takes place when the rotating sensing pattern encounters a flaw in a sub-layer of a multi-layer non-ferrous workpiece such as found in an aircraft splice joint.

BRIEF DESCRIPTION OF THE DRAWINGS

For a more complete understanding of the present invention and for further objects and advantages thereof, references may be made to the following description taken in conjunction with the accompanying drawings in which:

FIG. 4, is a central axis view of a hollow toroid driving core with the mounted polar coordinates sensor shown in cross-sectional view illustrating the first embodiment of a coupling coefficient of coupling means utilizing a gap in the driving flux path.

FIG. 5, is a radial view of the mounted polar coordinates sensor of FIG. 4.

FIG. 6, is a cross-sectional view of the second embodiment of a coupling coefficient means utilizing a conical pick-up core and conical bore in the driving core to vary a gap in the driving flux path.

POLAR COORDINATES SENSOR BASICS

Figure 1:
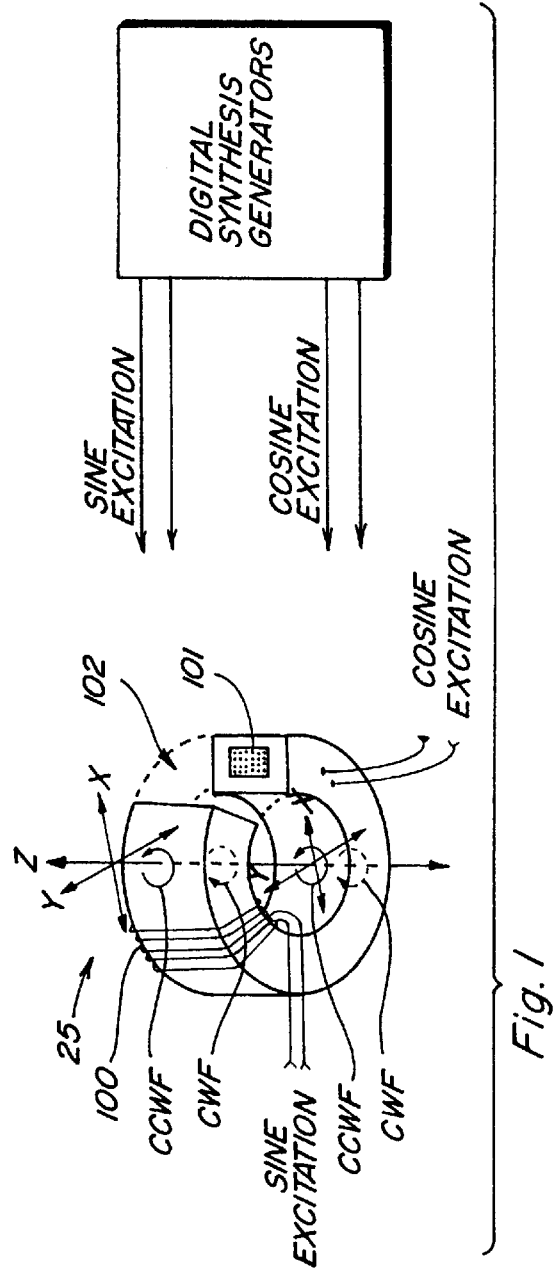
FIG. 1, is a perspective view of a hollow toroid core illustrating a basic rotating field driving core for driving a polar coordinates sensor.

To review now the fundamentals of polar coordinates sensors as described in the above listed patents. Referring now to FIG. 1, a hollow toroid core 25 of ferromagnetic material, is shown in cross-sectional view, the cut-away section is 102. There is an inside excitation winding 101, having connecting leads labeled COSINE EXCITATION. There is also an outside excitation winding 100 wound around the outside of hollow toroid 25, having connecting leads labeled SINE EXCITATION. The block labeled DIGITAL SYNTHESIS GENERATORS in FIG. 1, will be fully described in the Sine-Cosine Generators section. When sine-cosine excitation is applied to the inside and outside excitation windings a rotating magnetic field is induced throughout the entire toroid, the cumulative effect of the rotating magnetic dipoles. The axis of each magnetic dipole being perpendicular to the surface of core 25 everywhere, i.e. a magnetic dipole appears to rotate about any arbitrarily chosen center.

Figure 2:
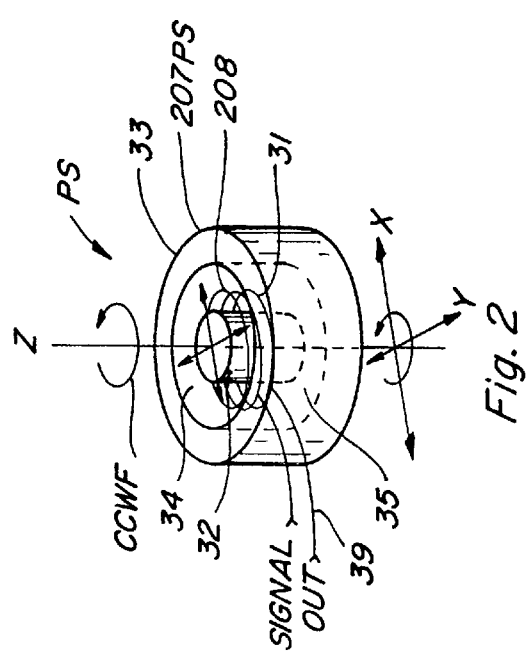
FIG. 2, is a perspective view of a basic polar coordinates sensor.

Referring again to FIG. 1, the relative rotational directions at four points on a diameter-wise line through hollow toroid 25 are illustrated by the CWF and CCWF arrows. FIG. 2 is a perspective view of the basic polar coordinates sensor 207PS (PS) illustrating the structural detail. A central pole 32 is concentrically surrounded by a cylindrical outer pole 33, providing an annular pick-up coil space 34. Poles 32 and 33 are connected by a base portion 35; this pick-up core is formed of a high permeability ferromagnetic material such as ferrite. A signal coil 208 is wound around the central pole 32.

Figure 3:
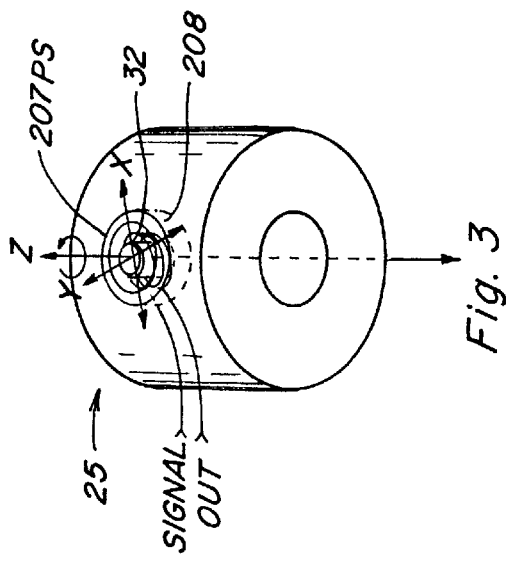
FIG. 3, is a perspective view of a polar sensor mounted partially within a bore formed in the outer circumference wall of a hollow toroid driving core.

FIG. 3 is a perspective view of polar coordinates sensor (polar sensor) mounted partially within a bore formed in the outer circumference wall of driving core 25 (the excitation windings are not shown for clarity). The Z-axis of polar sensor PS being perpendicular to the central axis of driving core 25. Notice that the windings of pick-up coil 208 are coplanar to the driving flux generated within the hollow toroid. The hollow toroid driving core 25 is normally operated near the magnetic saturation level, consequentially the annular shaped reduction in the driving core wall presented by the pick-up coil space provides a hemispherical fringing flux sensing pattern. With no target (workpiece) present the fringing sensing pattern is magnetically balanced and there is no flux linkage to pick-up coil 208. In this application the polar circle (sensing face) is referenced in terms of azimuth degrees.

DEFINITIONS AND ABBREVIATIONS

Polar Sensor (PS): The sensing assembly comprising a pick-up core and one or more pick-up coils, signal phase angle represents target (flaw) azimuth direction and signal amplitude represents target mass or flaw size.

Driving core: The sine-cosine excited core that drives the polar coordinates sensor (may take the form of a hollow toroid, a cross-shaped core, induction motor stator or other shapes).

THE COEFFICIENT OF COUPLING FACTOR

The first factor in the disclosed combination is the magnetic circuit path between the driving core and the pick-up core.

It is a well known fact in radio circuits such as r-f and i-f transformers that selectivity vs. frequency is dependent on the flux coupling factor (coefficient of coupling) between primary and secondary windings. As the coupling is made tighter, the bandwidth increases, at the expense of less gain for the resonant frequency. It is likewise known, a critical coupling gives the greatest signal gain and best selectivity.

As taught in the basics of polar coordinates sensors the pick-up coil is spatially oriented coplanar to the rotating driving flux i.e. a perfectly balanced sensing pattern generates a signal null because there is no net flux linkage to the pick-up coil.

FIGS. 4, 5 illustrate a first embodiment of a polar coordinates sensor PS1 utilizing a coupling coefficient means, having an annular gap 31 in the the driving flux path. FIG. 4 is a central axis view of driving core 55 and also a mounted polar coordinates sensor comprising a pick-up core 207 and a pick-up coil 208. The driving core 55 has an inside excitation winding 201 and an outside excitation winding 200. The only thing different in arrangement in this embodiment of polar coordinates sensing device is the coupling coefficient provided by the annular flux gap 31 as seen in FIGS. 4, 5. The diameter of bore 40 in the driving core wall is intentionally made slightly larger than the outside diameter of the pick-up core 207. This diameter difference may be better seen in FIG. 5, which is a radial view of the mounted polar coordinates sensor PS. The width of the flux gap is small, in the range of less than 0.01", this gap width (diameter difference between bore 40 and pick-up core 207) may be sized for the workpiece characteristics sought. FIG. 6 is a cross-section view of the second embodiment of a polar coordinates sensor PS2 having an adjustable flux coupling coefficient. The pick-up core 307 has a cone shaped outer circumference 311, the cone tapering toward the base portion 35. This cone shaped outer circumference is disposed concentric partially within a cone shaped bore 312 formed in a hollow toroid driving core 55A; this same cone shaped coupling arrangment may also be adapted for other driving core embodiments. Pick-up core 307 may be adjusted axially 313 to vary the flux coupling coefficient, the adjustment means may take the form of small screws 314 in the washer-like nonferrous magnetic shield MS that fits tightly around the sensing face end of the pick-up core 307. An alternative to screw adjustment means would be a plastic cone shim in the annular flux gap.

Figure 7:
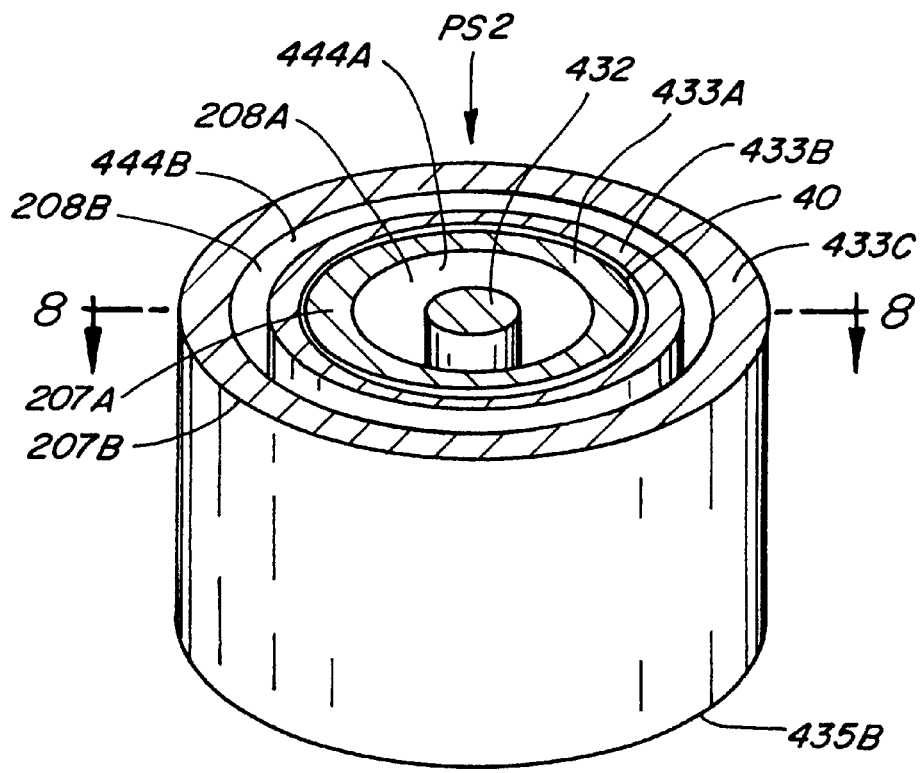
FIG. 7, is a perspective view of the third embodiment of a coupling coefficient means utilizing a hybrid poly-phase polar coordinates sensor arrangement with an annular gap in the driving flux path.
Figure 8:
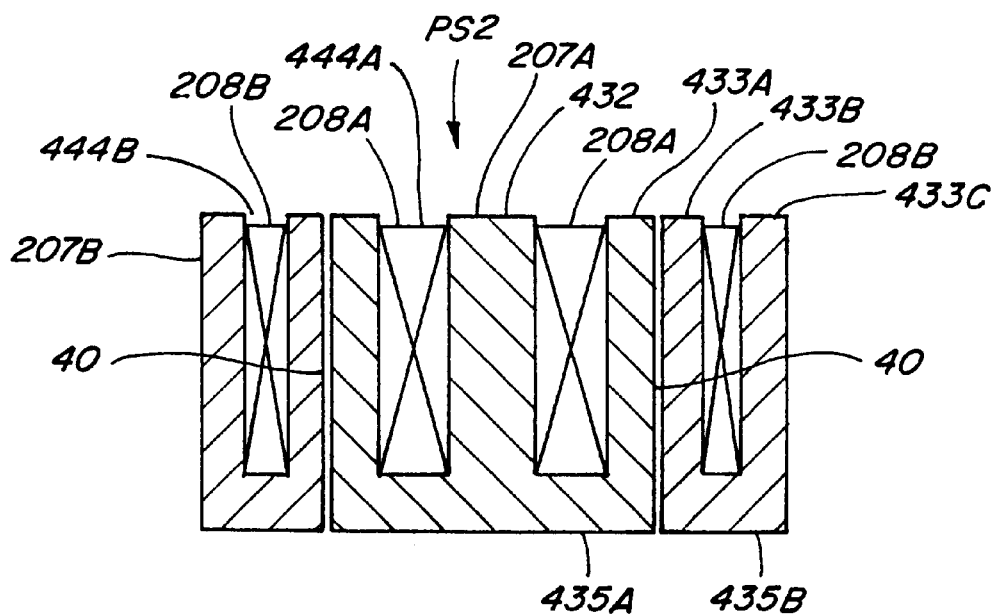
FIG. 8, is a cross-sectional view of the hybrid poly-phase polar coordinates sensor of FIG. 7 showing the two element pick-up core structure.

Many other means of adjusting the axial position 313 of pick-up core 307 may come to mind to the mechanically minded. Concentricity of the pick-up core within the bore, and coplanarity of the pick-up coil to the driving flux are of primary importance. FIG. 7 is a perspective view of the third embodiment of a polar coordinates sensor PS2 having a flux coupling coefficient. FIG. 8 is a cross-sectional view of PS2.

PS2 is a hybrid of the poly-phase embodiment polar sensor first disclosed in the Logue U.S. Pat. No. 5,404,101 and the single-phase embodiment polar sensor. There is a first pick-up core 207A formed of a high permeability material, that is identical to the pick-up core previously described in the basics section having an annular pick-up space 444A within which is wound a first pick-up coil 208A. Pick-up core 207A has a central cylindrical pole 432, an outer cylindrical pole 433A and a base portion 435A.

Concentrically surrounding pick-up core 207A is a second pick-up core 207B formed of a high permeability material having an annular pick-up coil space 444B, within which is wound a second pick-up coil 208B. Pick-up core 207B has an outer cylindrical pole 433C which is disposed partially within a bore formed in the driving core (as taught in the basics section). Pick-up core 207B also has an intermediate cylindrical pole 433B and a connecting base portion 435B. Pick-up cores 207A and 207B are separated by an annular flux gap 40 to provide a coefficient of coupling between the two. Annular flux gap 40 can be sized for critical coupling by selecting diameter ratios. A plastic material filled in the annular flux gap 40 may be used to concentrically support the inner pick-up core 207A within outer pick-up core 207B. The outer pick-up core 207B may be tightly fit in the driving core bore, this would provide a signal from pick-up coil 208B having a tight coupling coefficient of coupling and a signal from pick-up coil 208A having a loose coupling coefficient coupling for comparison purposes.

Figure 9:
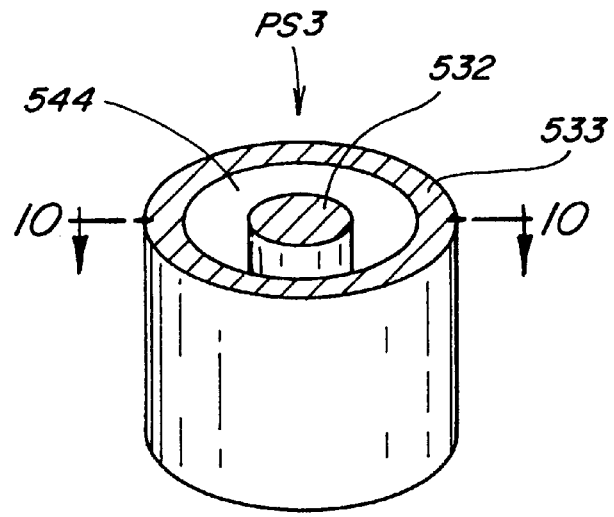
FIG. 9, is a perspective view of the fourth embodiment of a polar coordinates sensor with a coupling coefficient means utilizing an annular gap in the base portion of the driving core.
Figure 10:
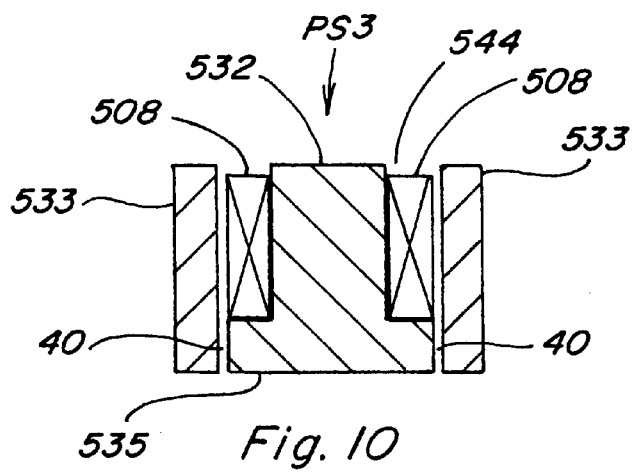
FIG. 10, is a cross-sectional view of the polar coordinates sensor of FIG. 9.
Figure 11:
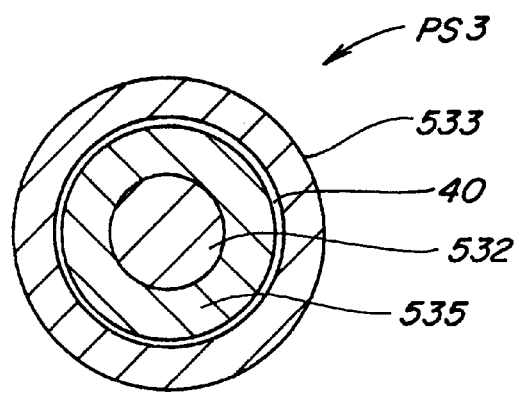
FIG. 11, is a radial view of the sensing face of the polar coordinates sensor of FIGS. 9, 10.

FIG. 9 is a perspective view of a fourth embodiment of a polar coordinates sensor PS3 utilizing an annular flux gap to provide a degree of flux coupling coefficient. There is an outer cylindrical pole 533 which fits partially within a bore formed in the driving core, this outer cylindrical pole being formed of a high permeability ferromagnetic material. There is also a central cylindrical pole 532 having a cylindrical base portion 535 which is shown in FIG. 10 (a cross-section view), both base 535 and central pole 532 being formed of high permeability material. FIG. 11 is an annular sensing face view of PS The annular flux gap 40 is seen in FIGS. 10, 11. Pick-up coil 508 is wound around central cylindrical pole 532. The outer cylindrical pole 533 may be fit tightly in the driving core bore to provide more driving flux to the workpiece while still having a critical coefficient of coupling. It is important to note concerning the four coupling coefficient embodiments shown, the pick-up coil(s) and pick-up core(s) are magnetically symmetrically balanced with no workpiece present or when the surface of an unflawed workpiece is exactly perpendicular to the sensing face axis.

THE "TANK-CIRCUIT" FACTOR

Figure 12:
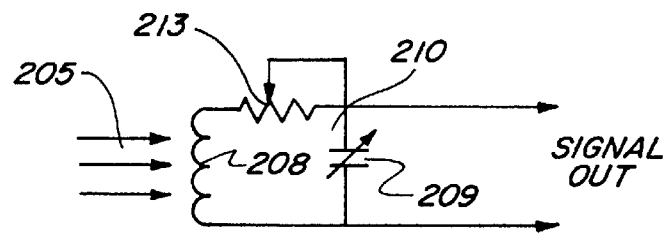
FIG. 12, is a schematic diagram of a series resonant tank circuit that illustrates the second factor of the subject combination.

The second factor of the disclosed combination is a capacitor connected across the pick-up coil terminals. The addition of this capacitor was first disclosed in the Logue U.S. Pat. No. 5,404,101, col. 6, Lines 67–68, and col. 7, lines 1–5, that circuit being illustrated in FIG. 12. Analyzing the circuit in FIG. 12 we see a series resonant circuit comprising the polar coordinates sensor pick-up coil 208 shunted by a capacitor 209. The capacitance of 209 may be a variable device for convenience of tuning or a fixed device of a predetermined value. The driving flux 205 is represented by lines drawn orthogonal to the pick-up coil axis i.e. coplanar to the pick-up coil turns. The resonant frequency of tank circuit 210 is related to: a) The ratio of XL to XC. b) The circuit Q affects the "flywheel" action or the sharpness of resonance. As the pick-up coil resistance increases the resonance curve becomes flatter, this series resistance factor may be made ajustable further by adding a variable resistor 213 in the tank circuit.

The Q of the tank circuit and the critical coupling coefficient to the driving flux allow the driven polar sensor (PS) to be more dependent on the eddy current reflection from first and second layers to unbalance the sensing pattern, than conventional mutual flux linkage methods. Different values of capacitance may be switched in or out of the disclosed tank circuit to obtain the desired range of signal frequencies (relating to depth resolution).

THE DRIVING FREQUENCY SPECTRUM FACTOR

Figure 13:
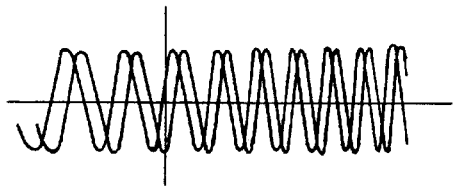
FIGS. 13–20 are actual oscilloscope pictures of the generated polar coordinates signals, FIG. 13 being the sine-cosine excitation and FIGS. 14–20 illustrating the polar coordinate sensor output signal response.

The third factor in the disclosed combination is the response of the polar coordinates sensor to a driving frequency change i.e. frequency modulation of the sine-cosine excitation currents suppling power to the driving core. This mode of excitation is intended to be used with any or all of the driving cores disclosed in previous and future patent applications to implement the objectives of the invention. FIG. 13 is an oscillscope picture of the sine-cosine excitation wave form illustrating the ramping of the frequency spectrum (800–1100 HZ). This excitation frequency modulation take several modes such as: 1. Ramping the frequency up at a predetermined constant rate over a predetermined range, followed by ramping the frequency down at the same predetermined rate. 2. Ramping the frequency up at a first rate over a predetermined range and then ramping down at a second rate over a predetermined range. 3. The sine-cosine excitation frequency is modulated according to a sine function over a predetermined range.

The cornerstone of multi-layer resolution is quadature excitation in which the frequency varies as a function of time.

ACTION OF THE COMBINATION

Definitions

Driving Frequency: The frequency of the sine-cosine excitation applied to the driving core.

Driving Spectrum: Shape of the driving frequency change, comprising: 1) length 2) rate of frequency change e.g. linear ramp, sinusoidal or other shapes.

Azimuth Heading: Location on the polar coordinates sensing face of the pick-up core is referenced in azimuth headings.

Signal Waveforms Generated by the Combination

In order to present the true nature of the output signals generated by the invention, the applicant will utilize actual oscilloscope trace pictures of the excitation and generated signal waveforms in FIGS. 13–20.

The dual trace sine wave voltages in FIG. 13 are the sine-cosine excitation voltages supplied to the polar coordinates sensor driving core (as explained in basics). Notice the two sine wave voltages are displaced by 90 degrees, and the frequency is ramping up at a linear rate (800–1100 HZ approx.). It has been discovered, ramping the sine-cosine excitation frequency up or down generates a frequency conversion process in the output signal. This sine-cosine excitation frequency modulation method was first filed under Disclosure Document No. 401663 Jun. 17, 1996, and second under Disclosure Document No. 406005 Sep. 20, 1996.

Figure 14:
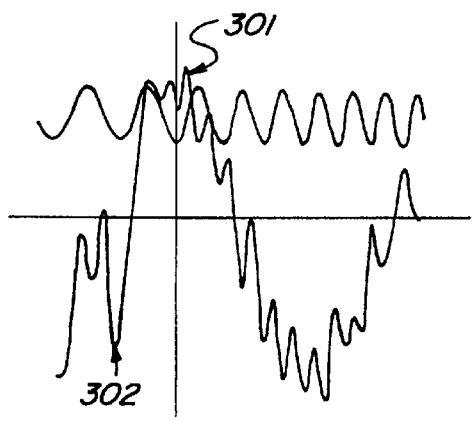

This unique frequency conversion process is related to a flaw located in a sub-layer of a multi-layer non-ferrous workpiece. The dual trace waveforms in FIG. 14 show one of the sine-cosine excitation reference voltages (top trace) and the polar sensor output signal (bottom trace).

Analyzing the polar coordinate signal (bottom trace in FIG. 14) which is generated in response to a flaw in the second layer of a multi-layer workpiece (two sheets of 0.100" thick aluminum), we see the signal contains two basic components i.e. a high frequency component and a low frequency component. The low frequency component has a positive peak 301 and a negative peak 302. To further illustrate this frequency conversion, refer now to FIGS. 15, 16, which are actual oscilloscope pictures of the polar sensor response to a multi-layered nonferrous workpiece (two sheets of 0.100" thick aluminum) utilizing all three factors of the subject combination. The sine-cosine excitation frequency ramping down (1100–800 HZ).

Figure 15:
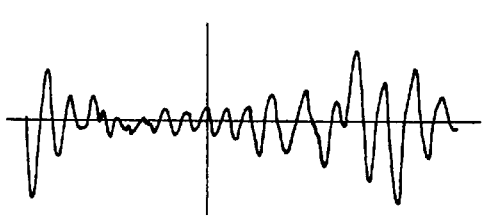

FIG. 15 is the signal response to an unflawed portion of the workpiece, the sensor axis being perpendicular to the plane of the workpiece. Notice the signal contains the driving frequency and some third harmonics, this being the signal null condition for an unflawed workpiece. A more perfect null is believed possible with more perfect prototype construction. Sensitivity apears to go up as a perfect null is approached. The word "flaw" in the remainder of this description is intended to include both cracks and corrosion thinning.

Figure 16:
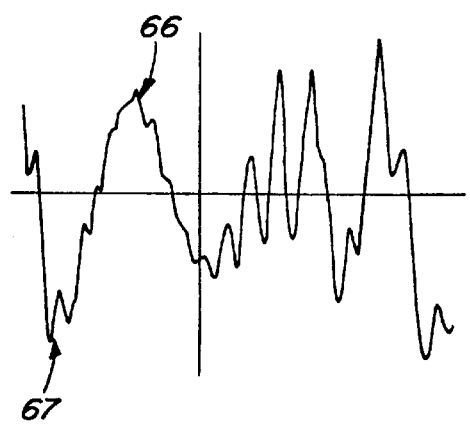

Referring now to FIG. 16, a crack in the second layer is positioned over the 270 degree azimuth of the sensing face and the resultant signal waveform is generated. Analyzing FIG. 16, we see the generated signal has: (1) a first sinusoidal component having a frequency equal to the excitation frequency. The phase angle of this first component shifts over a 360 degree range. The phase angle and amplitude of this first sinusoidal component primarly indicates first layer characteristics e.g. phase angle representing sensor axis angle to the workpiece/flaw in the first layer. (2) a second sinusoidal component having a sub-multiple frequency related to the rate of change of the sine-cosine excitation frequency (angular velocity). This sub-multiple frequency component has a positive peak 66 and a negative peak 67. Notice the sub-multiple component is not generated until a second layer flaw is present over the sensing face. Greatest signal amplitude is obtained when a crack is aligned radially relative go the probe axis. The phase angle of this sub-multiple frequency indicates the azimuth heading of the second layer flaw over the sensing face. The oscilloscope x-y settings are the same for FIGS. 15–20 to convey flaw response.

Notice in FIGS. 16–20, the positive and negative peaks of the sub-multiple component appear to be built up in discrete steps by the driving frequency. Tests on prototypes with a 2" flat search coil with many turns (untuned) on the far side of a 0.100" thick sheet of aluminum (search coil eccentric to sensing face) generates a very clean signal. Signal amplitude contains two basic components: (a) approx. 10 percent driving frequency component. (b) approx. 90 percent sub-frequency component. (c) the 10 percent driving frequency component is ridding on top of the 90 percent sub-frequency component. (d) there is a 360 degree phase shift range of the sub-frequency component corresponding to search coil eccentricity relative to the azimuth heading. e) there is no sub-frequency generated with a constant frequency sine-cosine excitation. Conclusion: the second layer is subjected to a sub-multiple inductive action much lower in frequency than the lowest driving core excitation frequency.

Figure 17:
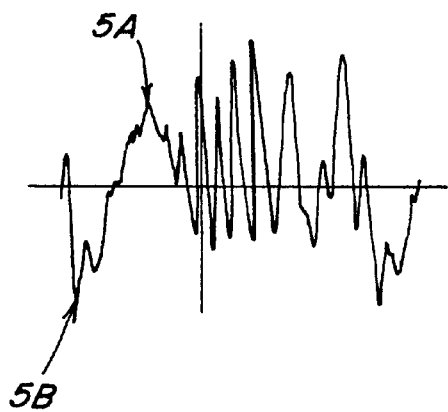
Figure 18:
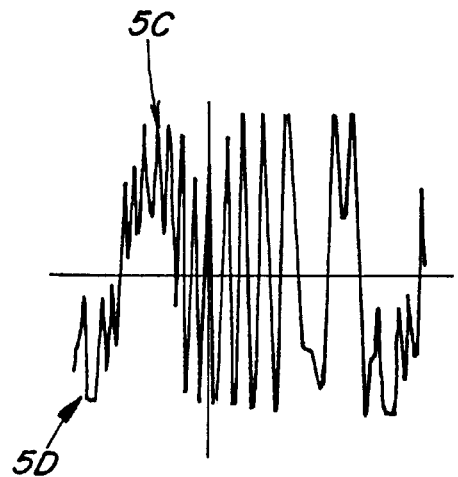

Another very advantageous characteristic of the invention is: tilting the polar sensor (PS) axis away several degrees from perfect perpendicularity to the plane of the first layer does not cause a loss of the sub-frequency component (second layer flaw indicator). The inventor has tilted the polar sensor (PS) axis at least 5 degrees off perpendicularity (in any azimuth heading) without sub-frequency component loss. This tilt ability is illustrated in FIGS. 17–20. In FIG. 17 the flaw is over the 270 degree azimuth of the sensing face, wherein the sub-frequency component positive peak is ref. No. 5A and the negative peak is ref. No. 5B. In FIG. 18 the polar sensor axis (the Z-axis in FIG. 2) is tilted at least 5 degrees out of perpendicularity on the x-coordinate (refer to FIG. 2). Analyzing FIG. 18, we see the positive excursion 5C contains the driving frequency component (indicating first layer off perpendicularity) superimposed on the sub-frequency component (second layer flaw indicator). The negative excursion 5D also contains both driving frequency and sub-frequency components.

Figure 19:
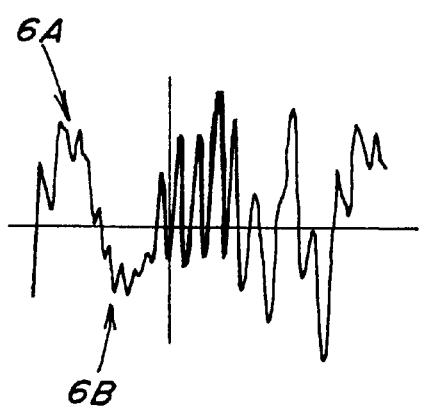
Figure 20:
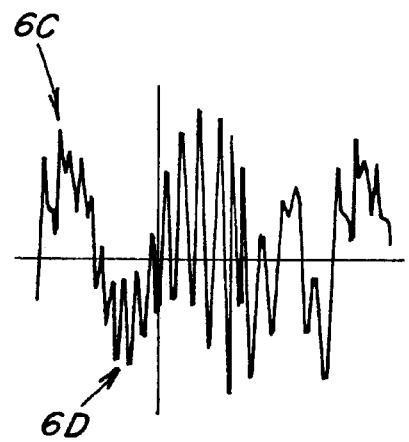

To further illustrate this unique flaw signal retention, refer to FIGS. 19, 20. In FIG. 19 a second layer flaw is over the 90 degree azimuth of the polar sensor generating a sub-frequency component 180 degrees out of phase compared to FIG. 17. In FIG. 19, 6A is the positive peak and 6B is the negative peak of the second layer flaw signal. In FIG. 20 the polar sensor axis is tilted at least 5 degrees out of perpendicularity on the y-coordinate (refer to FIG. 2). Analyzing the polar coordinates signal in FIG. 20, we see the positive excursion 6C contains the driving frequency component (indicating first layer out of perpendicularity) superimposed on the sub-frequency component (second layer flaw indication). The negative excursion 6D contains both the driving frequency and sub-frequency components, i.e. first layer perpendicularity and second layer flaw indicator (sub-frequency).

It is contemplated the disclosed frequency modulation method has special usefulness in enhancing the spatial resolution of the elliptical sensing pattern disclosed in the related patent application Ser. No. 08/599,775 entitled: "Method for Generating a Rotating Elliptical Sensing Pattern". Considering the driving frequency spectrum is extended i.e. both the ellipse generation (individual ellipse) and the ellipse precession go through an acceleration process (either positive or negative). Although initial research in testing the disclosed combination has been with nonferrous workpieces, its utility is also directed toward ferrous workpieces and composite materials.

LIFT-OFF

As earlier claimed the flaw signal is not lost (waveform shape is retained) e.g. when testing two layers of sheet aluminum 100 mils thick each. When the sensor to workpiece spacing is increased at least 100 mils (0.1") the flaw waveform (shown in FIGS. 16, 17, 19) does not change, only the amplitude decreases. Said another way the driving frequency and the sub-frequency (second layer flaw component) retains the original phase angles.

Even a variable spacing between layers (at least 60 mils) does not cause a loss of flaw waveshape (retains phase angles).

SINE-COSINE GENERATORS

The rotating sensing pattern is generated by digital synthesis means. Values of the sine-cosine excitation waveforms are stored in digital memory "look up tables". The look up tables are sequentially read at a high rate into two digital-to-analog converters which produce two "staircase" approximations of the sine-cosine waveforms including frequency spectrum (frequency modulation). This type of sine-cosine excitation is shown in FIG. 1, as block labled DIGITAL SYNTHESIS GENERATORS. Cloutier et al U.S. Pat. No. 5,418,460 teaches a voltage controlled oscillator being swept across a predetermined frequency range by a ramp generator. Warren et al U.S. Pat. No. 4,282,487 discloses a voltage controlled oscillator sweeping an excitation signal over a selected frequency range. The Logue U.S. Pat. No. 5,793,204 utilizes "look-up tables" that are sequentially read at a high rate into two digital-to-analog converters which produce two "staircase" approximations of the amplitude modulated sine and cosine waveforms.

SIGNAL PROCESSING

Processing the polar coordinates signal may take the form of Fourier analysis to map out the location of a flaw in multi-layered workpieces, utilizing state of the art digital hardware and software.

I claim:

1. A combination of elements for producing a sub-frequency conversion signal in a polar coordinates sensor, the said combination of elements comprising:

a) a hollow toroid driving core formed of a ferromagnetic material, the hollow toroid forming a torus wall with inside and outside surfaces, and;

i) a first excitation winding wound within the hollow toroid for inducing a first magnetic field throughout the said driving core;

ii) a second excitation winding wound around the outside of the hollow toroid for inducing a second magnetic field throughout the said driving core;

iii) sine-cosine excitation being applied to the first and second excitation windings for inducing a rotating driving field throughout the said driving core, and;

iv) a bore formed in the said torus wall, the axis of said bore being perpendicular to the said inside and outside surfaces;

b) a polar coordinates sensor comprising:

i) a pick-up core formed of a ferromagnetic material, further comprising:

ii) a central cylindrical magnetic pole, a cylindrical outer magnetic pole concentrically surrounding the central cylindrical magnetic pole on a common axis and radially spaced apart to provide an annular pick-up coil space, and;

iii) a base portion for connecting these magnetic poles at one end, the end opposite the base portion forming an annular sensing face, said annular sensing face being perpendicular to the common axis;

iv) a pick-up coil having multiple turns wound around the central cylindrical magnetic pole for generating said signal;

v) the said polar sensor being mounted coaxially within the said bore leaving the sensing and an extending portion outside the said torus wall, the turns of the pick-up coil being coplanar to the said driving field;

c) a coefficient of coupling between the said pick-up core and the said driving core by diameter differences between said bore and said cylindrical outer magnetic pole forming an annular air gap, and;

d) a resonant "tank-circuit" comprising a variable capacitor connected across the said pick-up coil forming a tunable series resonant circuit;

e) frequency modulation of the said sine-cosine excitation by digital synthesis means for generating the said sub-frequency conversion signal.

* * * * *